United States Patent [19]
Wiltrout et al.

[11] Patent Number: 5,282,745
[45] Date of Patent: Feb. 1, 1994

[54] DENTAL HANDPIECE PURGING DEVICE

[75] Inventors: John C. Wiltrout; Nora M. Wiltrout, both of Chippewa Falls, Wis.

[73] Assignee: Dental Components, Inc., Newberg, Oreg.

[21] Appl. No.: 38,854

[22] Filed: Mar. 29, 1992

[51] Int. Cl.[5] .............................................. A61C 1/10
[52] U.S. Cl. ....................................... 433/114; 433/132
[58] Field of Search ...................... 433/104, 114, 132

[56] References Cited

U.S. PATENT DOCUMENTS

| | | | |
|---|---|---|---|
| 3,106,021 | 10/1963 | Borden | 433/104 |
| 3,494,110 | 2/1970 | Reed et al. | 433/114 |
| 4,544,355 | 10/1985 | Eibofner et al. | 433/104 |
| 4,877,399 | 10/1989 | Frank et al. | 433/132 |

Primary Examiner—John J. Wilson
Attorney, Agent, or Firm—James D. Divnan, Jr.

[57] ABSTRACT

A housing of the device receives a pressurized air flow which is filtered and directed past a pressure reducing valve prior to delivery to a purge valve assembly. The purge valve assembly includes a connector configured for endwise engagement with the specific handpiece being purged. The connector is removably mounted in the purge valve assembly which also includes a valve member displaced by the connector during a purging operation from a spring biased closed position. Various connectors are interchangeable to adapt the device to service a variety of dental handpieces.

6 Claims, 1 Drawing Sheet

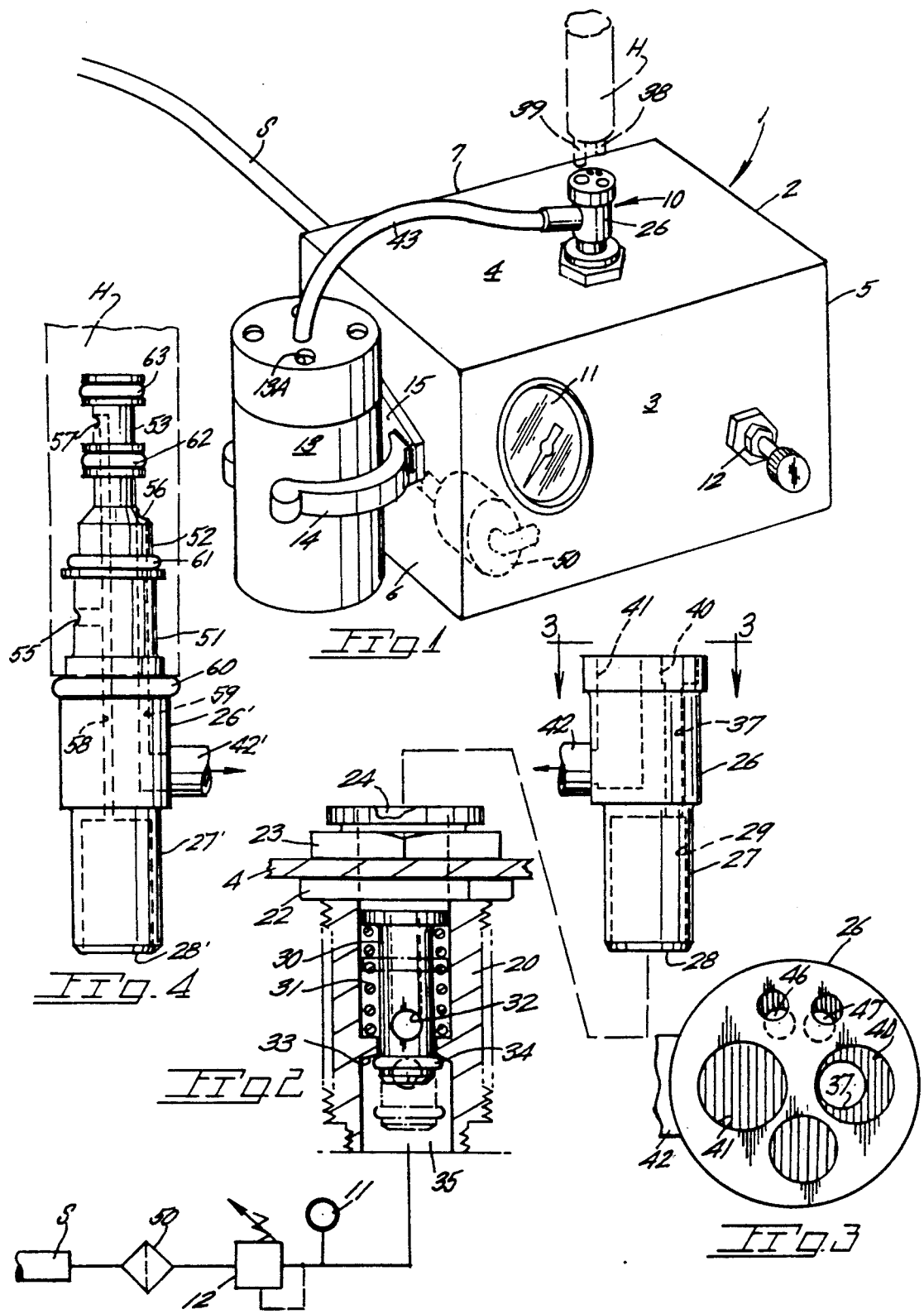

DENTAL HANDPIECE PURGING DEVICE

BACKGROUND OF THE INVENTION

The present invention pertains generally to equipment for servicing of dental handpieces.

For optimum life and operation of dental handpieces it is recommended by the various manufacturers that same be cleaned and lubricated on a daily basis in addition to autoclaving. Currently dental handpieces are being serviced preparatory to autoclaving by the temporary coupling of a pressure hose to the handpiece and the manual actuation of a valve control to administer a reduced pressurized airflow to the handpiece. The pressurized airflow enters the handpiece passageways, normally carrying during use both an air and water flow, to purge same of any debris or lubricant being forcefully ejected from the handpiece. The repeated steps in coupling several dental handpieces to a pressure hose and the actuation of an air valve by a technician takes considerable time each day. Further, particles discharged from a handpiece during purging can be ejected at considerable velocity. Further, as air pressure used for purposes of purging can be 50 psi or so the connection between hose and handpiece must be made positive manner to avoid accidental separation.

SUMMARY OF THE PRESENT INVENTION

The present invention is embodied within dental equipment for use in a dental office which enables momentary coupling of a dental handpiece to a source of pressurized air with such coupling enabling rapid thorough purging of the dental handpiece.

A housing of the present device carries an adaptor serving to connect the multiple conduits of a dental handpiece with a source of pressurized air to clear the passageways to purge the primary passageway serving the turbine motor of the handpiece to remove foreign matter and any excess lubricant directed to a receptacle. Additionally the adaptor serves to direct pressurized secondary airflows to the water passageway and the air passageway of the handpiece. Momentary engagement of a dental handpiece with the adaptor and subsequent downward displacement of same serves to connect the handpiece with a source of pressurized air for purging of handpiece passageways. Subsequent to such purging, the handpiece is typically autoclaved. The adaptor is received within a valve body having a spring biased member which automatically closes the valve body in the absence of a manually depressed handpiece biasing the adaptor downwardly into the valve body. As dental handpiece configurations will vary between models and manufacturers the present invention includes adaptors of various internal configurations for coupling with such an array of handpieces. An air pressure reducing valve permits the present device to utilize line pressures typically higher than that required for purging of dental handpieces. A receptacle assures confinement of purged foreign matter.

Important objectives of the present invention include the provision of a compact device permitting a person to rapidly service a number of dental handpieces in some instances both prior and after autoclaving; the provision of a device wherein a dental handpiece may be momentarily inserted into an adaptor and both the handpiece and adaptor displaced to open a valve member of the device for the admission of pressurized multiple airflows to the handpiece and the routing of discharged air to a receptacle; the provision of a dental device which permits purging of dental handpieces at the optimum pressure as recommended by their manufacturer regardless of line pressure in the dental office; the provision of a device wherein purging of a dental handpiece necessitates only the coupling of the handpiece to an adaptor to effect a considerable time savings.

BRIEF DESCRIPTION OF THE DRAWINGS

In the accompanying drawings:

FIG. 1 is a perspective view of the present invention;

FIG. 2 is a sectional view of a purge valve assembly removed from the housing of the device with an air supply shown in schematic form;

FIG. 3 is a plan view of the adaptor of the present device taken along line 3—3 of FIG. 2; and FIG. 4 is a vertical elevational view of a modified form of adaptor usable with still another type of handpiece;

DETAILED DESCRIPTION OF THE PREFERRED EMBODIMENTS

With continuing attention to the drawings wherein applied reference numerals indicate parts similarly hereinafter identified the present device is indicated generally at 1 and includes a housing 2.

Housing 2 includes a frontal wall 3 and a top wall 4 with side walls at 5 and 6 and a rear wall at 7. A purge valve assembly is indicated generally at 10 supported in place on a wall of the housing to receive the end of a handpiece at H. The valve assembly is described below.

A pressure gage 11 along with an air pressure reducing valve 12 may be located in front wall 3 of the housing for convenience sake while a receptacle at 13 is removably supported in place by a pair of yieldable arms 14 on a bracket 15 in place on a housing wall.

With attention again to purge valve assembly 10 the same includes a valve body 20 for securement in place on housing wall 4 as by means of a nut 22. A flange 23 of the valve body abuts the housing wall 4 with valve body 20 terminating upwardly therefrom to define an open end of a socket 24. An adaptor at 26 has a lower, tubular portion 27 which slidably engages socket 24 to permit a lower end 28 of the adaptor to be received in valve body 20 within socket 24. End 28 engages a valve stem 30. Valve stem 30 is spring biased upwardly by a spiral spring 31 to a closed position whereat a port 32 in the stem is offset upwardly from a valve seat 33 against which an O-ring 34 on the stem seats. Downward displacement of valve stem 30 brings port 32 into pressurized area 35 of the valve assembly. Adapter 26 constitutes a connector to receive the handpiece.

The adaptor at 26 may be as shown in FIG. 2 or otherwise configured as, for example, as shown in FIG. 4 to suit the particular make and model of handpiece being serviced.

Adaptor 26 includes a passageway 37 through which a pressurized flow of air passes when stem 30 is depressed to the broken line portion of FIG. 2. The handpiece H shown in FIG. 1 is of the type having an air inlet projection at 38 and an air exhaust outlet at 39. Accordingly, for purging such a handpiece, air is discharged from adaptor passageway 37 (FIG. 2) into handpiece drive air inlet 38 momentarily seated in a socket 40 in the upper end of the adaptor. Similarly, a handpiece drive air outlet 39 is seated within a socket 41 of the adaptor which permits outlet air from the handpiece to enter the adaptor and be discharged via a nipple 42 to which is secured a discharge conduit 43. With attention to FIG. 3 it will be seen that secondary air passages at 46 and 47 are also in communication with pressurized area 29 of the adaptor for the purpose of directing air flows through both the cooling air and cooling water passageways (not shown) of the handpiece. Pressurized air passing through the coolant air and water passageways of the handpiece exhaust via the outlets in the head of the handpiece.

In housing 2, a filter at 50 is of the metal mesh type with a filtering capability of 35 microns or so. Pressure reducing valve at 12 permits servicing of the present device with 90-100 psi commonly provided in dental office air systems at S which is reduced to 30-50 psi, depending on the handpiece manufacturers requirements, to avoid damage to the handpiece. Excess lubricant applied to the handpiece during preparation of the handpiece will be expelled and collected in container 13. Openings 13A vent the container.

With attention to the modified adaptor or connector at 26' in FIG. 4 such is for use in servicing that type of dental handpiece H having an elongate opening in its base. Those parts of the modified connector 26' corresponding to those parts of the earlier described connector 26 are identified by like prime reference numerals. A series of annular walls 51, 52 and 53 are axially spaced along an insertable segment of the connector and are of differing diameters with the walls having ports 55, 56 and 57 with port 57 discharging a flow of drive air, port 56 receiving a return flow of drive air and port 55 discharging air for purging the cooling air and water passages of the handpiece. In the modified adaptor a combination drive air and air/water passageway is at 58 with ports at 55 and 57 to exhaust air from passageway 58 into inlet orifices in the handpiece. Port 56 receives return drive air for routing to an outlet nipple 42', via a passageway 59. O-rings as at 60, 61, 62 and 63 isolate the areas served by the above noted ports during a purging operation.

In use, the handpiece handle is endwise engaged with connector 26—26' and urged downwardly against the action of spring 31 to reposition port 32 into communication with pressurized air in inlet area 35 of valve assembly 10. The air flow entering the handpiece passageways will serve to deposit lubricant on turbine motor components as well as displace foreign matter from air-water passageways or excess lubricant. Manufacturers of the handpieces each have their particular servicing requirements.

While we have shown but a few embodiments of the invention, it will be apparent to those skilled in the art that the invention may be embodied still otherwise without departing from the spirit and scope of the invention.

Having thus described the invention, what is desired to be secured by a Letters Patent is:

We claim:

1. A device for purging dental handpieces of the type having communicating air inlet and air outlet passageways, said device comprising,
   a housing including wall members,
   a receptacle,
   a purge valve assembly carried by said housing for communication with a source of pressurized air and including a connector for engagement with one end of a handpiece, said connector defining an air outlet for pressurized air and a pressurized air inlet for respective communication with the inlet and the outlet passageways of the handpiece, a valve member controlling a pressurized air flow from said source to said outlet of said connector for purging the handpiece passageways, biasing means urging said valve member toward a closed position, said connector in downstream communication with said receptacle via a conduit for delivery of matter purged from the handpiece.

2. The device claimed in claim 1 wherein said connector is in rested engagement with said valve member.

3. The device claimed in claim 1 wherein said connector comprises means for manual displacement of said valve member by a hand held handpiece momentarily in downwardly biased engagement with the connector.

4. The device claimed in claim 1 wherein said housing includes a settable pressure reducing valve and an air pressure gage.

5. The device claimed in claim 1 wherein said connector includes an insertable segment for inserted engagement with said handpiece, said segment having axially spaced circular seals therealong for contact with the handpiece.

6. A device for purging dental handpieces of the type having a turbine and communicating turbine drive air inlet and turbine drive air outlet passageways, said device comprising,
   a housing including wall members, and
   a purge valve assembly carried by said housing for communication with a source of pressurized air and including a connector for engagement with one end of a handpiece, said connector defining an air outlet for pressurized air and a pressurized air inlet for respective communication with the turbine drive air inlet and the turbine drive air outlet passageways of the handpiece, a valve member in said housing controlling a pressurized air flow from said source to said outlet of said connector for purging the turbine and the handpiece passageways, biasing means urging said valve member toward a closed position, said connector in rested engagement with said valve member.

* * * * *